United States Patent [19]

Heckele

[11] Patent Number: 4,832,004
[45] Date of Patent: May 23, 1989

[54] LARYNGOSCOPE FOR LASER TREATMENT

[75] Inventor: Helmut Heckele, Knittlingen, Fed. Rep. of Germany

[73] Assignee: Richard Wolf, GmbH, Fed. Rep. of Germany

[21] Appl. No.: 36,794

[22] Filed: Apr. 10, 1987

[30] Foreign Application Priority Data

Apr. 16, 1986 [DE] Fed. Rep. of Germany ....... 3612783

[51] Int. Cl.$^4$ .............................................. A61B 1/26
[52] U.S. Cl. .................................... 128/10; 128/303.1
[58] Field of Search ....................... 128/4, 6, 7, 10, 11, 128/12, 17, 303.1, 9

[56] References Cited

U.S. PATENT DOCUMENTS

| | | | |
|---|---|---|---|
| 2,243,285 | 5/1941 | Pope | 128/6 |
| 2,483,233 | 9/1949 | Price et al. | 128/17 |
| 3,091,235 | 5/1963 | Richards | 128/6 |
| 3,261,350 | 7/1966 | Wallace | 128/6 |
| 4,126,127 | 11/1978 | May | 128/11 |
| 4,211,229 | 7/1980 | Warster | 128/303.1 |
| 4,470,407 | 9/1984 | Hussein | 128/303.1 |
| 4,622,967 | 11/1986 | Schachar | 128/9 |

FOREIGN PATENT DOCUMENTS

| | | | |
|---|---|---|---|
| 3431179 | 3/1985 | Fed. Rep. of Germany. | |
| 1424893 | 2/1976 | United Kingdom | 128/10 |
| 2156217 | 10/1985 | United Kingdom | 128/10 |

OTHER PUBLICATIONS

Richard Wolf GmbH Sales Sheet, "MV-OP-Laryngoskop G/Rhino-Laryngologi 31/XI. 82d", 1982.

Primary Examiner—Richard C. Pinkham
Assistant Examiner—Mark S. Graham
Attorney, Agent, or Firm—Hill, Van Santen, Steadman & Simpson

[57] ABSTRACT

A laryngoscope for laser treatment of the larynx comprises a hollow shaft, a hollow handle on the proximal end of the shaft communicating with the hollow inside of the shaft, a coupling on the handle for an angularly adjustable chest support and a hose connector stub or the like on the coupling or the handle for applying suction via the handle and the shaft to remove smoke and/or steam from the operating site at the distal end of the shaft.

2 Claims, 2 Drawing Sheets

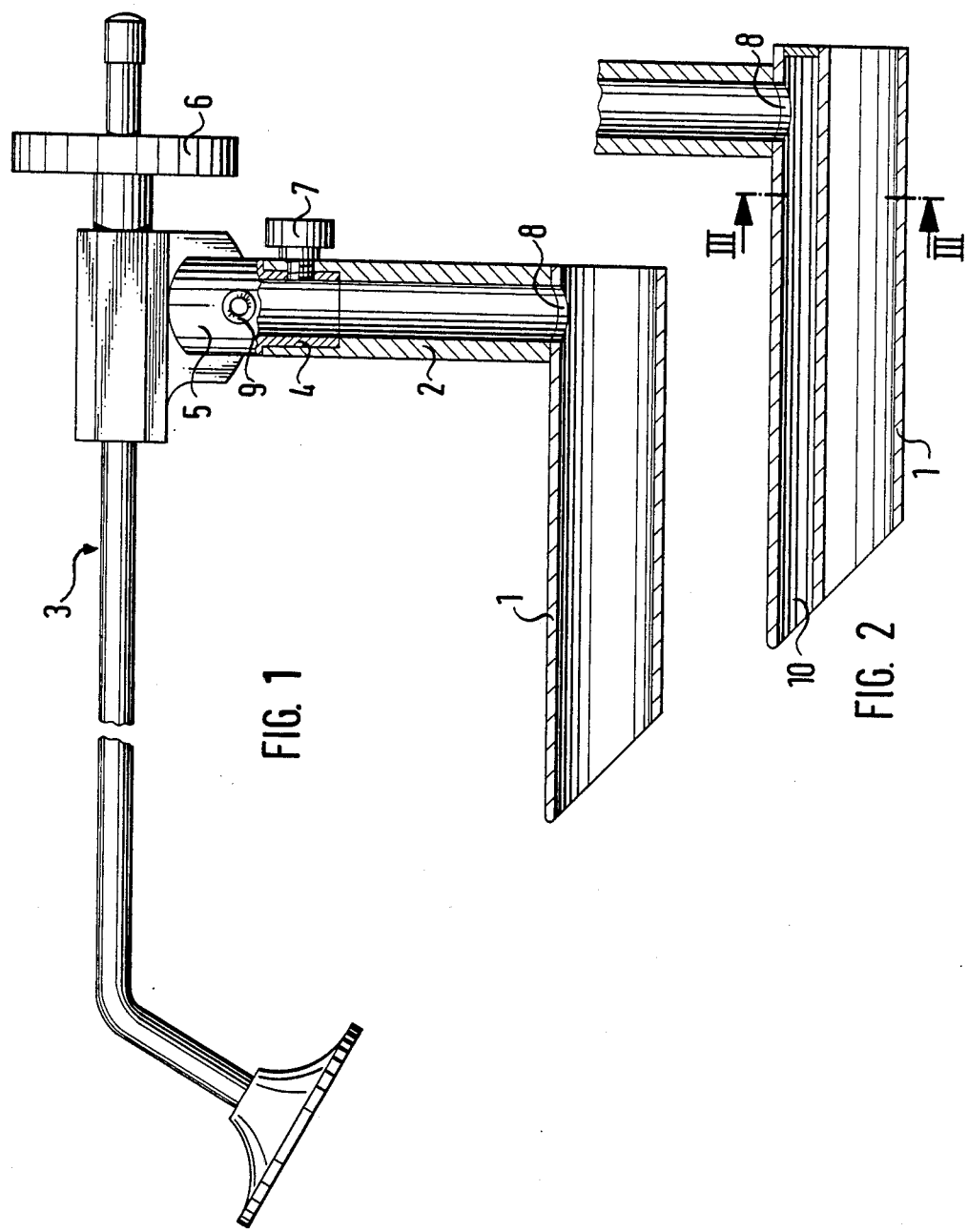

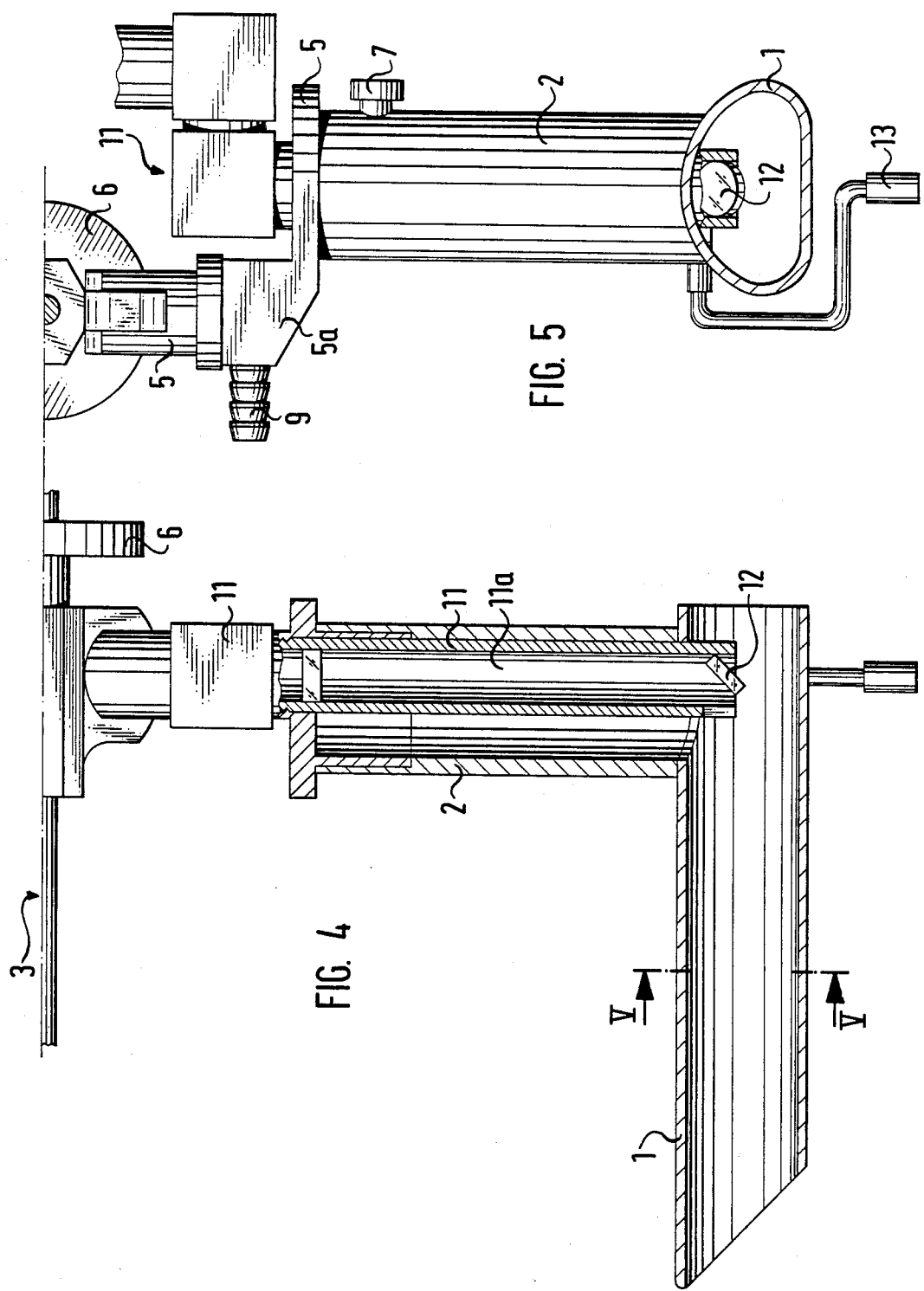

LARYNGOSCOPE FOR LASER TREATMENT

BACKGROUND OF THE INVENTION

1. Field of the Invention

The invention relates to a laryngoscope for laser treatment of the larynx, comprising a shaft having a proximal end provided with an angled-over handle whose free extremity has releasably connected to it a coupling member connectible to the handle, which has a joint for a pivotally adjustable chest support.

2. Description of the Prior Art

In the case of such known laryngoscope smoke and/or steam, which greatly obstructs the view of the operating surgeon, are generated at the site of the operation by tissue coagulation by means of the laser beam. This generation of steam and/or smoke, which may be carcinogenic, also results in considerable discomfort of the operating surgeon.

SUMMARY OF THE INVENTION

It is accordingly an object of the invention to provide means of removing the smoke and/or steam generated during endoscopic laser treatment by means of laryngoscopes.

In the case of a laryngoscope of the kind referred to in the foregoing, this object is achieved in that in the proximal terminal section, the laryngoscope has a shaft connected to the internal volume of a hollow handle attached thereto which may be connected to a vacuum pump through a tube or hose connector stub and a hose pipe, either direct or via the coupling member.

Using the laryngoscope of the invention, the smoke and/or steam generated during the laser treatment may be drawn off by means of the pump, via the unobstructed passage of the laryngoscope shaft, via the handle and the pipe connector.

Since the smoke and/or steam may be distributed unevenly over the free cross-section of the laryngoscope shaft during withdrawal by suction, according to a preferred embodiment of the invention a suction drain channel extends through the laryngoscope shaft from the distal extremity to the connector leading to the internal volume of the handle. The smoke and/or steam generated at the locus of the operation by the laser treatment may thereby be drawn off by suction direct at the site of the operation, so that obstructions can no longer occur within the laryngoscope shaft and that a nuisance is no longer caused by carcinogenic smoke components.

According to the invention, it is advantageous to construct the coupling between the chest support and the handle in such manner that the focussing system of a laser also extends through the coupling member, the laser beam then being directed through the laryngoscope shaft by means of an adjustable deflection means, as will be described in particular in the following.

Further objects and advantages of the invention will become apparent from the following detailed description when read with reference to the accompanying drawings.

BRIEF DESCRIPTION OF THE DRAWINGS

FIG. 1 is an axial cross-sectional view with portions in elevation of the laryngoscope with a handle and chest support being coupled thereto;

FIG. 2 is a partial axial cross sectional view through the laryngoscope with a modified suction channel for smoke removal;

FIG. 3 is a cross-sectional view taken on line III—III of the laryngoscope shaft of FIG. 2;

FIG. 4 is an axial cross-sectional view through a laryngoscope comprising a laser connector, in accordance with a further embodiment of the invention; and FIG. 5 is a cross-sectional view taken along the line V to V of FIG. 4.

DESCRIPTION OF THE PREFERRED EMBODIMENTS

In the embodiment of FIG. 1, the laryngoscope comprises a shaft 1 and a hollow handle 2, which has a chest support 3 connected to it via a coupling member 5 engaging with a tube extension 4 into the end of the handle remote from the shaft and angularly adjustable by means of a pivotal handle 6. The coupling member 5 may be fixedly secured to the handle 2 by means of a clamping screw or other known device.

According to the invention, the shaft 1 is proximally connected via an aperture 8 to the internal volume of the hollow handle 2 and this handle space is connected to a vacuum pump which is not illustrated either direct or, advantageously, via a hose connector 9 of the coupling member 5 and a hose pipe. If tissue coagulations are then performed at the distal extremity of the shaft 1 by means of a laser beam, the smoke and/or steam concomitantly generated may be drawn off by suction by means of the vacuum pump. Visibility is retained thereby for the operating surgeon. In this connection, the possibility exists however that smoke and/or stem may spread unevenly over the shaft cross-section, so that the view of the operating surgeon is then partially obstructed. To secure a clear view in all cases, in the modified embodiment shown in FIGS. 2 and 3 a suction drain channel 10 is provided along the upper cross-sectional portion, through the shaft 1 from the distal extremity, said channel being joined at its proximal extremity to the hollow handle 2 via the perforation 8. It is thereby possible for the smoke and/or steam developed at the locus of operation to be drawn off by suction at the very locus of operation, thereby securing a clear view for the operating surgeon at all times.

So that a fixed coordinate between the laser and the laryngoscope may be obtained during treatment by means of a laser, in the embodiment illustrated in FIGS. 4 and 5 a laser focussing means 11 is combined with the laryngoscope.

In this embodiment the coupling member 5 is offset angularly and laterally with respect to the axis of the handle, so that the hose connector 9 and the pivot spindle of the chest support 3 are also offset laterally, whereas the angled-over section 5a is then traversed by a part of the laser focussing system in the form of a space 11a, which at its free lower extremity comprises a deflection device 12, e.g. a reflector, whereby the laser beam is adjustably deflectible and may be aimed at the tissue at the distal extremity of the shaft 1, which is to be coagulated. The adjustment of the reflector may be performed by means of a handle 13.

What is claimed is:

1. In a laryngoscope for laser treatment of the larynx, said laryngoscope having a hollow shaft with a hollow handle attached in fluid communication to said shaft at a proximal end of the shaft and projecting at an angle thereto, said handle at a free end being provided with a coupling part, said coupling part having an articulation for pivotably and adjustably mounting a chest support, the improvements comprising a focusing insert for a laser, a proximal end region of the laryngoscope shaft being connected to a source of suction via the coupling part of the handle to draw a suction through the shaft and handle, said coupling part for the connection of the chest support and the source of suction being laterally offset relative to an axis of the handle, said coupling part providing a mounting for the focussing insert, said focussing insert including a tubular part extending from the mounting through the length of said handle and terminating in a reflector disposed in said shaft so that a laser beam proceeding through the insert in the handle is reflected into said hollow shaft.

2. In a laryngoscope according to claim 1, wherein the coupling part includes a hose connector stud for connecting a hose from a source of suction to said laryngoscope.

* * * * *